US010624837B2

(12) United States Patent
Deng et al.

(10) Patent No.: US 10,624,837 B2
(45) Date of Patent: Apr. 21, 2020

(54) FOOD-GRADE LIP BALM AND PREPARATION METHOD THEREOF

(71) Applicant: I&B (GUANGZHOU) BIOLOGICAL TECHNOLOGY CO., LTD., Guangzhou, Guangdong (CN)

(72) Inventors: Weijian Deng, Guangdong (CN); Xumin Huang, Guangdong (CN); Jinxiong Lin, Guangdong (CN); Minghua Zhang, Guangdong (CN)

(73) Assignee: I&B (GUANGZHOU) BIOLOGICAL TECHNOLOGY CO., LTD., Guangzhou (CN)

( * ) Notice: Subject to any disclaimer, the term of this patent is extended or adjusted under 35 U.S.C. 154(b) by 0 days.

(21) Appl. No.: 16/111,442

(22) Filed: Aug. 24, 2018

(65) Prior Publication Data

US 2020/0022904 A1 Jan. 23, 2020

(30) Foreign Application Priority Data

Jul. 18, 2018 (CN) .......................... 2018 1 0794954

(51) Int. Cl.
*A61K 36/00* (2006.01)
*A61K 8/92* (2006.01)
*A61K 8/49* (2006.01)
*A61Q 19/00* (2006.01)

(52) U.S. Cl.
CPC .............. *A61K 8/922* (2013.01); *A61K 8/498* (2013.01); *A61Q 19/001* (2013.01); *A61K 2800/805* (2013.01)

(58) Field of Classification Search
None
See application file for complete search history.

(56) References Cited

U.S. PATENT DOCUMENTS

2005/0281851 A1* 12/2005 Cap ........................ A61K 8/922 424/401
2010/0151060 A1* 6/2010 Magee ................ A61K 8/0229 424/727

FOREIGN PATENT DOCUMENTS

CN 104546644 A 4/2015
CN 107137257 A * 9/2017
CN 107661275 A 2/2018

* cited by examiner

*Primary Examiner* — Qiuwen Mi

(57) ABSTRACT

The present invention relates to a food-grade lip balm and the preparation method thereof, and belongs to the field of skin care products. The food-grade lip balm of the present invention comprises the following components: 1-30 parts by weight of rice bran wax, 10-80 parts by weight of shea butter, 1-60 parts by weight of a hydrogenated vegetable oil, 2-50 parts by weight of a naturally derived emollient oil, 0.1-30 parts by weight of a naturally derived aromatic oil, and 0.1-10 parts by weight of tocopherol. The components of the lip balm of the present invention are all naturally derived. It is safe and has good lip-protecting effects. The food-grade lip balm is of natural origin, safe and moisturizing; it has good ductility and moisture retention ability, could effectively tackle the drying and peeling of the lip skin, and provides a good user experience.

15 Claims, No Drawings

FOOD-GRADE LIP BALM AND PREPARATION METHOD THEREOF

CROSS REFERENCE TO RELATED APPLICATIONS

The present application claims the benefit of Chinese Patent Application No. 201810794954.2 filed on Jul. 18, 2018. All the above are hereby incorporated by reference.

FIELD OF THE INVENTION

The invention relates to a food-grade lip balm and the preparation method thereof, and belongs to the field of skin care products.

BACKGROUND OF THE INVENTION

Lip balm is a common skin care product used in daily life. It is mainly used to tackle the loosening, drying and peeling of the lip skin. Most of the lip balms currently on the market contain non-naturally-derived ingredients; they especially contain petroleum-derived oils and waxes as their main ingredients. When being used, part of the lip balm staying on the lips will enter the body through various activities including drinking and eating. The long-term and abundant use of lip balms with petroleum-derived oils and waxes as their main ingredients is unhealthy, and may readily lead to lip allergies: the lip skin may crack, peel, redden and itch; in more severe cases, it may even lead to lesions and cancer, threatening human health.

Chinese Patent Application No. 201410814282.9 has disclosed a lipstick, which comprises fat, a natural excipient and a wax. The wax is a pure plant-extracted wax; the fat is naturally extracted. The lipstick comprises 35-40 parts of the pure plant-extracted wax, 55-65 parts of the naturally extracted oil, and 2.5-5.5 parts of the natural excipient. Naturally extracted ingredients were employed in this application to provide a lip balm that keeps the lips moisturized and elastic. However, its effects did not extend to the tackling of cracked lip skin.

Chinese Patent Application No. 201711080665.8 has disclosed a scented lip balm of pure natural origin, which is composed of the following components in percentage by weight: (1) 60%-90% of a naturally derived emollient oil; (2) 5%-40% of a naturally derived solid wax; (3) 0.01%-5% of a naturally derived antioxidant; (4) 0.01%-10% of a naturally derived aromatic oil; (5) 0.01%-5% of a naturally derived color; (6) 0.01%-5% of a naturally derived active ingredient. It can be seen that all components of the lip balm disclosed in patent application No. 201711080665.8 are naturally derived. A number of components were introduced in order to obtain a highly safe and effective lip balm. However, the ductility of the lip balm was not mentioned.

SUMMARY OF THE INVENTION

The objective of the present invention is to overcome the shortcomings of the prior art stated above, and to provide a food-grade lip balm that is of natural origin, safe and moisturizing; said food-grade lip balm has good ductility and moisture retention ability, could effectively tackle the drying and peeling of the lip skin, and provides a good user experience. The present invention also provides a preparation method of the food-grade lip balm.

To achieve the objective above, the technical solution of the present invention is:

A food-grade lip balm, which comprises the following components:

1-30 parts by weight of rice bran wax, 10-80 parts by weight of shea butter, 1-60 parts by weight of a hydrogenated vegetable oil, 2-50 parts by weight of a naturally derived emollient oil, 0.1-30 parts by weight of a naturally derived aromatic oil, and 0.1-10 parts by weight of tocopherol.

The rice bran wax is 100% derived from rice and does not contain any additives. Shea butter is obtained from the seeds of shea fruits, which is of western African origin; as high as 17% of the shea butter's content is unsaponifiable; it can prevent skin dryness, skin diseases, eczema, dermatitis, and sunburn. The hydrogenated vegetable oil is a very stable vegetable oil with good moisturizing effect; it not only gives an ideal texture and a suitable viscosity to skin care and cosmetic products, improves the ductility of these products, but also retains skin moisture, protects skin and promotes skin regeneration. The naturally derived emollient oil gives a long-lasting moisturizing effect; it can rapidly increase the water content of the stratum corneum, activate the metabolic activity of epidermal cells, increase the collagen content of skin, and absorb ultraviolet light. It can be used in sunscreens and after sun repair products; it soothes inflammation, treats allergies, and regenerates a healthy stratum corneum layer. It is especially suitable for dry skin, aging skin and sensitive skin. The naturally derived aromatic oil is used in skin care products; it is easily absorbed by the skin and does not leave oil stains. It is the gentlest and safest way to tackle the drying and peeling of the skin. When used in lip products, it can soothe chapped lips and help restore the vitality of the lip skin. Tocopherol is a major oil-soluble antioxidant that protects the lipoproteins and unsaturated fatty acids in the cell membrane against effects exerted by oxygen and free radicals produced by pollution. It can be added to various cosmetic products for anti-oxidation; it is an excellent natural antioxidant.

Chinese Patent Application No. 201410814282.9 employed natural extracted ingredients to provide a lip balm that keeps the lips moisturized and elastic. However, its effects did not extend to the tackling of cracked lip skin. Chinese Patent Application No. 201711080665.8 had included a number of components in order to achieve its objective, but the ductility of the lip balm was not mentioned.

As a preferred embodiment of the food-grade lip balm of the present invention, the lip balm comprises the following components:

10 parts by weight of the rice bran wax, 40 parts by weight of the shea butter, 5 parts by weight of the hydrogenated vegetable oil, 30 parts by weight of the naturally derived emollient oil, 10 parts by weight of the naturally derived aromatic oil, and 5 parts by weight of the tocopherol.

According to research, when employing 10 parts by weight of rice bran wax, 40 parts by weight of shea butter, 5 parts by weight of a hydrogenated vegetable oil, 30 parts by weight of a naturally derived emollient oil, 10 parts by weight of a naturally derived aromatic oil, and 5 parts by weight of tocopherol, the lip balm obtained is safer, more moisturizing, could more effectively tackle the drying and peeling of the lip skin, provides better user experience, and has better ductility and moisture retention ability.

As a preferred embodiment of the food-grade lip balm of the present invention, the hydrogenated vegetable oil is selected from at least one of hydrogenated avocado oil, hydrogenated olive oil, hydrogenated shea butter, hydrogenated rapeseed oil, hydrogenated soybean oil, and hydrogenated sunflower oil.

As a preferred embodiment of the food-grade lip balm of the present invention, the naturally derived emollient oil is selected from at least one of olive fruit oil, corn oil, rapeseed oil, sesame seed oil, sunflower seed oil, wild soybean oil, and avocado oil.

As a preferred embodiment of the food-grade lip balm of the present invention, the naturally derived emollient oil is the olive fruit oil.

As a preferred embodiment of the food-grade lip balm of the present invention, the naturally derived aromatic oil is selected from at least one of coconut oil, peppermint oil, rose oil, lemon oil, and lavender oil.

As a preferred embodiment of the food-grade lip balm of the present invention, the naturally derived aromatic oil is the coconut oil. Coconut oil contains a high proportion of medium chain fatty acids, of which lauric acid accounts for about 50%; it also contains octanoic acid (C8), decanoic acid (C10) and the like. The presence of short length and medium length carbon chains gives the product a unique skin feel and is more skin friendly. The coconut oil obtained by cold pressing completely retains the original fragrance of the coconut, which could replace the addition of artificial fragrance. As a result, the formula is less stimulating and more natural.

The present invention also provides a method of preparing the food-grade lip balm described above, comprising the following steps:

(1) Adding rice bran wax, shea butter, a hydrogenated vegetable oil, a naturally derived emollient oil, and a naturally derived aromatic oil to a heating and mixing tank according to a predesignated ratio; heating and stirring;

(2) Cooling a mixture obtained in step (1) to 60° C.; adding tocopherol according to a predesignated ratio; stirring uniformly;

(3) Pouring a mixture obtained in step (2) into a mold; cooling, demolding, sterilizing and packaging the mixture to obtain the food-grade lip balm.

As a preferred embodiment of the method of preparing the food-grade lip balm of the present invention, in step (1), the stirring speed is 100 rpm, and the heating temperature is 80-85° C.

Comparing with the prior art, the beneficial effects of the present invention are as follows:

The components of the lip balm of the present invention are all naturally derived. It is safe and has good lip-protecting effects. Naturally derived aromatic oil is added to provide a pleasant smell, giving a good user experience. The food-grade lip balm is of natural origin, safe and moisturizing; it has good ductility and moisture retention ability, could effectively tackle the drying and peeling of the lip skin, and provides a good user experience.

DETAILED DESCRIPTION OF THE ILLUSTRATED EMBODIMENTS

The objectives, technical solutions and advantages of the present invention will be described clearly and completely hereafter with reference to the embodiments.

Embodiment 1

A food-grade lip balm, comprising the following components: 1 part by weight of rice bran wax, 10 parts by weight of shea butter, 60 parts by weight of hydrogenated olive oil, 2 parts by weight of olive fruit oil, 30 parts by weight of coconut oil, and 0.1 parts by weight of tocopherol.

The method of preparing the food-grade lip balm of the present embodiment comprises the following steps:

(1) The rice bran wax, shea butter, hydrogenated olive oil, olive fruit oil, and coconut oil were added to a heating and mixing tank; stirring mode was started at a rate of 100 rpm; heating was turned on until the temperature reached 80-85° C.

(2) The mixture obtained in step (1) was cooled to 60° C.; tocopherol was added according to the predesignated ratio, and stirring was continued until uniform dispersion;

(3) The mixture obtained in step (2) was poured into a mold; it was then cooled, demolded, sterilized and packed to obtain the food-grade lip balm.

Embodiment 2

A food-grade lip balm, comprising the following components: 30 parts by weight of rice bran wax, 80 parts by weight of shea butter, 1 part by weight of hydrogenated olive oil, 50 parts by weight of olive fruit oil, 0.1 parts by weight of coconut oil, and 10 parts by weight of tocopherol.

The method of preparing the food-grade lip balm of the present embodiment is the same as that of embodiment 1.

Embodiment 3

A food-grade lip balm, comprising the following components: 10 parts by weight of rice bran wax, 40 parts by weight of shea butter, 5 parts by weight of a hydrogenated vegetable oil, 30 parts by weight of olive fruit oil, 10 parts by weight of coconut oil, and 5 parts by weight of tocopherol.

The method of preparing the food-grade lip balm of the present embodiment is the same as that of embodiment 1.

Embodiment 4

A food-grade lip balm, comprising the following components: 15 parts by weight of rice bran wax, 20 parts by weight of shea butter, 10 parts by weight of hydrogenated olive oil, 20 parts by weight of olive fruit oil, 20 parts by weight of coconut oil, and 2 parts by weight of tocopherol.

The method of preparing the food-grade lip balm of the present embodiment is the same as that of embodiment 1.

Embodiment 5

A food-grade lip balm, comprising the following components: 20 parts by weight of rice bran wax, 30 parts by weight of shea butter, 30 parts by weight of hydrogenated olive oil, 40 parts by weight of olive fruit oil, 15 parts by weight of coconut oil, and 7 parts by weight of tocopherol.

The method of preparing the food-grade lip balm of the present embodiment is the same as that of embodiment 1.

Embodiment 6

A food-grade lip balm, comprising the following components: 25 parts by weight of rice bran wax, 60 parts by weight of shea butter, 50 parts by weight of hydrogenated olive oil, 45 parts by weight of olive fruit oil, 25 parts by weight of coconut oil, and 9 parts by weight of tocopherol.

The method of preparing the food-grade lip balm of the present embodiment is the same as that of embodiment 1.

Embodiment 7

A food-grade lip balm, comprising the following components: 10 parts by weight of rice bran wax, 40 parts by weight of shea butter, 5 parts by weight of hydrogenated olive oil, 30 parts by weight of corn oil, 10 parts by weight of peppermint oil, and 5 parts by weight of tocopherol.

The method of preparing the food-grade lip balm of the present embodiment comprises the following steps:

(1) The rice bran wax, shea butter, hydrogenated olive oil, corn oil, and peppermint oil were added to a heating and mixing tank according to the predesignated ratio; stirring was started at a rate of 100 rpm; heating was turned on until the temperature reached 80-85° C.

(2) The mixture obtained in step (1) was cooled to 60° C.; tocopherol was added according to the predesignated ratio, and stirring was continued until uniform dispersion;

(3) The mixture obtained in step (2) was poured into a mold; it was then cooled, demolded, sterilized and packed to obtain the food-grade lip balm.

Embodiment 8

A food-grade lip balm, comprising the following components: 10 parts by weight of rice bran wax, 40 parts by weight of shea butter, 5 parts by weight of hydrogenated olive oil, 30 parts by weight of rapeseed oil, 10 parts by weight of rose oil, and 5 parts by weight of tocopherol.

The method of preparing the food-grade lip balm of the present embodiment comprises the following steps:

(1) The rice bran wax, shea butter, hydrogenated olive oil, rapeseed oil, and rose oil were added to a heating and mixing tank according to the predesignated ratio; stirring was started at a rate of 100 rpm; heating was turned on until the temperature reached 80-85° C.

(2) The mixture obtained in step (1) was cooled to 60° C.; tocopherol was added according to the predesignated ratio, and stirring was continued until uniform dispersion;

(3) The mixture obtained in step (2) was poured into a mold; it was then cooled, demolded, sterilized and packed to obtain the food-grade lip balm.

Embodiment 9

A food-grade lip balm, comprising the following components: 10 parts by weight of rice bran wax, 40 parts by weight of shea butter, 5 parts by weight of hydrogenated olive oil, 30 parts by weight of sesame seed oil, 10 parts by weight of lemon oil, and 5 parts by weight of tocopherol.

The method of preparing the food-grade lip balm of the present embodiment comprises the following steps:

(1) The rice bran wax, shea butter, hydrogenated olive oil, sesame seed oil, and lemon oil were added to a heating and mixing tank according to the predesignated ratio; stirring was started at a rate of 100 rpm; heating was turned on until the temperature reached 80-85° C.

(2) The mixture obtained in step (1) was cooled to 60° C.; tocopherol was added according to the predesignated ratio, and stirring was continued until uniform dispersion;

(3) The mixture obtained in step (2) was poured into a mold; it was then cooled, demolded, sterilized and packed to obtain the food-grade lip balm.

Comparative Embodiment 1

A food-grade lip balm, comprising the following components: 10 parts by weight of rice bran wax, 40 parts by weight of shea butter, 5 parts by weight of hydrogenated olive oil, 10 parts by weight of coconut oil, and 5 parts by weight of tocopherol.

The method of preparing the food-grade lip balm of the present embodiment comprises the following steps:

(1) The rice bran wax, shea butter, hydrogenated olive oil, and coconut oil were added to a heating and mixing tank according to the predesignated ratio; stirring was started at a rate of 100 rpm; heating was turned on until the temperature reached 80-85° C.

(2) The mixture obtained in step (1) was cooled to 60° C.; tocopherol was added according to the predesignated ratio, and stirring was continued until uniform dispersion;

(3) The mixture obtained in step (2) was poured into a mold; it was then cooled, demolded, sterilized and packed to obtain the food-grade lip balm.

Comparative Embodiment 2

A food-grade lip balm, comprising the following components: 10 parts by weight of rice bran wax, 40 parts by weight of shea butter, 30 parts by weight of olive fruit oil, 10 parts by weight of coconut oil, and 5 parts by weight of tocopherol.

The method of preparing the food-grade lip balm of the present embodiment comprises the following steps:

(1) The rice bran wax, shea butter, olive fruit oil, and coconut oil were added to a heating and mixing tank according to the predesignated ratio; stirring was started at a rate of 100 rpm; heating was turned on until the temperature reached 80-85° C.

(2) The mixture obtained in step (1) was cooled to 60° C.; tocopherol was added according to the predesignated ratio, and stirring was continued until uniform dispersion;

(3) The mixture obtained in step (2) was poured into a mold; it was then cooled, demolded, sterilized and packed to obtain the food-grade lip balm.

Comparative Embodiment 3

A food-grade lip balm, comprising the following components: 10 parts by weight of rice bran wax, 30 parts by weight of olive fruit oil, 10 parts by weight of coconut oil, and 5 parts by weight of tocopherol.

The method of preparing the food-grade lip balm of the present embodiment comprises the following steps:

(1) The rice bran wax, olive fruit oil, and coconut oil were added to a heating and mixing tank according to the predesignated ratio; stirring was started at a rate of 100 rpm; heating was turned on until the temperature reached 80-85° C.

(2) The mixture obtained in step (1) was cooled to 60° C.; tocopherol was added according to the predesignated ratio, and stirring was continued until uniform dispersion;

(3) The mixture obtained in step (2) was poured into a mold; it was then cooled, demolded, sterilized and packed to obtain the food-grade lip balm.

Comparative Embodiment 4

A food-grade lip balm, comprising the following components: 40 parts by weight of rice bran wax, 5 parts by weight of shea butter, 5 parts by weight of hydrogenated olive oil, 30 parts by weight of olive fruit oil, 10 parts by weight of coconut oil, and 5 parts by weight of tocopherol.

The method of preparing the food-grade lip balm of the present embodiment is the same as that of embodiment 1.

Comparative Embodiment 5

A food-grade lip balm, comprising the following components: 10 parts by weight of rice bran wax, 40 parts by weight of shea butter, 0.5 parts by weight of hydrogenated olive oil, 55 parts by weight of olive fruit oil, 10 parts by weight of coconut oil, and 5 parts by weight of tocopherol.

The method of preparing the food-grade lip balm of the present embodiment is the same as that of embodiment 1.

Evaluation 1

Hereafter describes an evaluation test for embodiments 1-9 and comparative embodiment 1-5.

420 volunteers of different genders, ages and from different regions were randomly selected and divided into 14 groups. The lip balms prepared in embodiment 1-9 and comparative embodiments 1-5 were continuously applied by each volunteer for 3 months. Then, the lip balms were rated by the volunteers on 4 different aspects using a score between 1 and 5, with 5 being the best and 1 being the worst. The results were averaged and rounded to one decimal place. The results are shown in Table 1.

TABLE 1

| | Moisturizing effect | Drying and cracking improvement effect | Ductility | Moisture retention ability |
|---|---|---|---|---|
| Embodiment 1 | 5 | 4.9 | 4.9 | 4.5 |
| Embodiment 2 | 5 | 4.9 | 4.8 | 4.7 |
| Embodiment 3 | 5 | 5 | 4.9 | 5 |
| Embodiment 4 | 5 | 4.8 | 4.9 | 4.7 |
| Embodiment 5 | 5 | 4.8 | 4.8 | 4.8 |
| Embodiment 6 | 5 | 4.9 | 4.8 | 4.7 |
| Embodiment 7 | 5 | 4.8 | 4.9 | 4.8 |
| Embodiment 8 | 5 | 4.9 | 4.8 | 4.9 |
| Embodiment 9 | 5 | 4.9 | 4.9 | 4.8 |
| Comparative embodiment 1 | 4.3 | 3.7 | 4.9 | 3.1 |
| Comparative embodiment 2 | 5 | 5 | 4.2 | 5 |
| Comparative embodiment 3 | 4.2 | 3.6 | 4.2 | 3.2 |
| Comparative embodiment 4 | 4.5 | 4.1 | 4.9 | 4.1 |
| Comparative embodiment 5 | 4.4 | 4.2 | 4.4 | 4.2 |

Comparative embodiment 2 did not contain hydrogenated olive oil. It exhibited good effects but poor ductility, the user experience is not good. Comparative embodiment 3 did not contain shea butter and hydrogenated olive oil; its ductility and the user experience were poor. In comparative embodiments 4 and 5, the weight percentages of rice bran wax, shea butter, olive fruit oil, coconut oil, and tocopherol were not all within the range of the present invention. From the results, it can be concluded that their effects were not as good as those of the present invention; the components of the food-grade lip balm, when combined together according to the parts by weight specified by the present invention, give the food-grade lip balms good moisturizing effect, good drying and cracking improvement effect, good ductility and good moisture retention ability. Furthermore, when the food-grad lip balm contained 10 parts by weight of rice bran wax, 40 parts by weight of shea butter, 5 parts by weight of hydrogenated olive oil, 30 parts by weight of olive fruit oil, 10 parts by weight of coconut oil, and 5 parts by weight of tocopherol, it exhibited the best moisturizing effect, drying and cracking improvement effect, ductility and moisture retention ability.

Evaluation 2

The acute oral toxicity testing of the food grade lip balm of the present invention is described hereafter.

Acute oral toxicity testing is the first step in assessing the toxicity of the raw materials of a skin care product. It can provide information on health hazards through short-term oral exposure. The test results can be used as the basis for toxicity classification, labeling of raw materials of skin care products, and determining the doses for subchronic toxicity tests and other toxicological tests.

Acute oral toxicity: the health-damaging effect occurred in a test animal in a short period of time, after the oral administration of a test substance to the test animal once or more than once within 24 hours.

Oral median lethal dose (LD50): a statistical dose of a test substance that causes the death of half of the experimental animals after one oral administration of the test substance. It is expressed in the weight of the test substance accepted by a unit body weight (mg/kg or g/kg).

Experimental Method

Mice of both sexes were randomly selected and randomly divided into 9 groups (one group for each of embodiments 1-9), 6 mice in each group. They were fasted for 16 hours without restricting their water intake. The groups were given the following doses of lip balms respectively: 0, 1000 mg/kg, 2000 mg/kg, 3000 mg/kg, 4000 mg/kg, and 5000 mg/kg. These lip balms were administered to the mice orally in one sitting. The general state, poisoning performance and death of the mice were closely observed and recorded for 1 week. After 1 week, the mice in each group were given water and food; their eating and drinking behavior was normal, no poisoning or death had occurred. Their skin, hair and eyes were normal, and there had been no tremor, convulsion, diarrhea or coma. In this test, the maximum dose group is 5000 mg/kg, and no animal death occurred, indicating that the oral median lethal dose is larger than 5000 mg/kg. According to the acute toxicity classification, it can be understood that this oral median lethal dose of ≥5000 mg/kg is not toxic in practice. Therefore, it can be concluded that the lip balms prepared in Examples 1 to 9 were not toxic.

Under the conditions of the present test, the oral median lethal dose (LD50) of the lip balms prepared in embodiments 1 to 9 of the present invention is LD50>5,000 mg/kg, which is a non-toxic grade.

It should be understood that the above embodiments are merely illustrative of the technical solutions of the present invention and are not intended to limit the scope of the present invention. The technical solutions of the present invention may be modified or equivalently substituted without departing from the spirit and scope of the technical solutions of the present invention.

What is claimed is:

1. A food-grade lip balm, which comprises the following components:

1-30 parts by weight of rice bran wax, 10-80 parts by weight of shea butter, 1-60 parts by weight of a hydrogenated vegetable oil, 2-50 parts by weight of a olive fruit oil, 0.1-30 parts by weight of a naturally derived aromatic oil, and 0.1-10 parts by weight of tocopherol.

2. The food-grade lip balm according to claim 1, which comprises the following components: 10 parts by weight of the rice bran wax, 40 parts by weight of the shea butter, 5 parts by weight of the hydrogenated vegetable oil, 30 parts by weight of the olive fruit oil, 10 parts by weight of the naturally derived aromatic oil, and 5 parts by weight of the tocopherol.

3. The food-grade lip balm according to claim 1, wherein the hydrogenated vegetable oil is selected from at least one of hydrogenated avocado oil, hydrogenated olive oil, hydrogenated shea butter, hydrogenated rapeseed oil, hydrogenated soybean oil, and hydrogenated sunflower oil.

4. The food-grade lip balm according to claim 1, wherein the naturally derived aromatic oil is selected from at least one of coconut oil, peppermint oil, rose oil, lemon oil, and lavender oil.

5. The food-grade lip balm according to claim 4, wherein the naturally derived aromatic oil is the coconut oil.

6. A method of preparing the food-grade lip balm according to claim 1, comprising the following steps:

(1) adding rice bran wax, shea butter, a hydrogenated vegetable oil, a olive oil fruit oil, and a naturally derived aromatic oil to a heating and mixing tank according to a predesignated ratio; heating and stirring;

(2) cooling a mixture obtained in step (1) to 60° C.; adding tocopherol according to a predesignated ratio; stirring uniformly;

(3) pouring a mixture obtained in step (2) into a mold; cooling, demolding, sterilizing and packaging the mixture to obtain the food-grade lip balm.

7. A method of preparing the food-grade lip balm according to claim 2, comprising the following steps:

(1) adding rice bran wax, shea butter, a hydrogenated vegetable oil, a olive fruit oil, and a naturally derived aromatic oil to a heating and mixing tank according to a predesignated ratio; heating and stirring;

(2) cooling a mixture obtained in step (1) to 60° C.; adding tocopherol according to a predesignated ratio; stirring uniformly;

(3) pouring a mixture obtained in step (2) into a mold; cooling, demolding, sterilizing and packaging the mixture to obtain the food-grade lip balm.

8. A method of preparing the food-grade lip balm according to claim 3, comprising the following steps:

(1) adding rice bran wax, shea butter, a hydrogenated vegetable oil, a olive fruit oil, and a naturally derived aromatic oil to a heating and mixing tank according to a predesignated ratio; heating and stirring;

(2) cooling a mixture obtained in step (1) to 60° C.; adding tocopherol according to a predesignated ratio; stirring uniformly;

(3) pouring a mixture obtained in step (2) into a mold; cooling, demolding, sterilizing and packaging the mixture to obtain the food-grade lip balm.

9. A method of preparing the food-grade lip balm according to claim 4, comprising the following steps:

(1) adding rice bran wax, shea butter, a hydrogenated vegetable oil, a naturally derived emollient oil, and a naturally derived aromatic oil to a heating and mixing tank according to a predesignated ratio; heating and stirring;

(2) cooling a mixture obtained in step (1) to 60° C.; adding tocopherol according to a predesignated ratio; stirring uniformly;

(3) pouring a mixture obtained in step (2) into a mold; cooling, demolding, sterilizing and packaging the mixture to obtain the food-grade lip balm.

10. A method of preparing the food-grade lip balm according to claim 5, comprising the following steps:

(1) adding rice bran wax, shea butter, a hydrogenated vegetable oil, a naturally derived emollient oil, and a naturally derived aromatic oil to a heating and mixing tank according to a predesignated ratio; heating and stirring;

(2) cooling a mixture obtained in step (1) to 60° C.; adding tocopherol according to a predesignated ratio; stirring uniformly;

(3) pouring a mixture obtained in step (2) into a mold; cooling, demolding, sterilizing and packaging the mixture to obtain the food-grade lip balm.

11. A method of preparing the food-grade lip balm according to claim 6, wherein in step (1), a stirring speed is 100 rpm, and a heating temperature is 80-85° C.

12. A method of preparing the food-grade lip balm according to claim 7, wherein in step (1), a stirring speed is 100 rpm, and a heating temperature is 80-85° C.

13. A method of preparing the food-grade lip balm according to claim 8, wherein in step (1), a stirring speed is 100 rpm, and a heating temperature is 80-85° C.

14. A method of preparing the food-grade lip balm according to claim 9, wherein in step (1), a stirring speed is 100 rpm, and a heating temperature is 80-85° C.

15. A method of preparing the food-grade lip balm according to claim 10, wherein in step (1), a stirring speed is 100 rpm, and a heating temperature is 80-85° C.

* * * * *